(12) United States Patent
McBride

(10) Patent No.: US 7,476,223 B2
(45) Date of Patent: Jan. 13, 2009

(54) BLADDER CATHETER SET

(75) Inventor: Barry McBride, Coleraine (IE)

(73) Assignee: Teleflex Medical Incorporated, Limerick, PA (US)

( * ) Notice: Subject to any disclaimer, the term of this patent is extended or adjusted under 35 U.S.C. 154(b) by 142 days.

(21) Appl. No.: 10/877,057

(22) Filed: Jun. 25, 2004

(65) Prior Publication Data

US 2005/0070882 A1     Mar. 31, 2005

(30) Foreign Application Priority Data

Jun. 27, 2003   (DE) .................. 103 29 128

(51) Int. Cl.
*A61M 5/00*     (2006.01)
*A61M 5/32*     (2006.01)
*B65D 81/24*    (2006.01)
*B65D 83/10*    (2006.01)
*B65D 1/34*     (2006.01)
*A61B 17/06*    (2006.01)

(52) U.S. Cl. .................. 604/544; 604/265; 604/172; 206/210; 206/364; 206/438; 206/571

(58) Field of Classification Search ................ 604/171, 604/172, 265–267, 540, 544, 327, 328; 206/210, 206/363, 364, 438, 571

See application file for complete search history.

(56) References Cited

U.S. PATENT DOCUMENTS

| | | | |
|---|---|---|---|
| 2,856,932 A | | 10/1958 | Griffitts |
| 3,154,080 A | * | 10/1964 | Rowan et al. ............ 604/171 |
| 3,898,993 A | | 8/1975 | Taniguchi |
| 3,967,728 A | * | 7/1976 | Gordon et al. ........... 206/364 |
| 4,091,922 A | * | 5/1978 | Egler ...................... 206/364 |
| 4,140,127 A | | 2/1979 | Cianci et al. |
| 4,204,527 A | | 5/1980 | Wu et al. |
| 4,754,877 A | * | 7/1988 | Johansson et al. ........ 206/364 |
| 4,811,847 A | * | 3/1989 | Reif et al. ............... 206/571 |
| 5,105,942 A | * | 4/1992 | van Veen et al. ......... 206/364 |
| 5,147,341 A | * | 9/1992 | Starke et al. ............. 604/349 |
| 5,226,530 A | * | 7/1993 | Golden .................... 206/210 |
| 5,454,798 A | | 10/1995 | Kubalak et al. |
| 6,065,597 A | * | 5/2000 | Pettersson et al. ........ 206/364 |
| 6,071,266 A | * | 6/2000 | Kelley .................... 604/265 |
| 6,090,075 A | * | 7/2000 | House .................... 604/172 |
| 6,355,004 B1 | | 3/2002 | Pedersen et al. |
| 6,736,805 B2 | * | 5/2004 | Israelsson et al. ........ 604/544 |
| 6,887,230 B2 | | 5/2005 | Kubalak et al. |
| 7,166,120 B2 | * | 1/2007 | Kusleika ................. 606/191 |
| 2005/0015076 A1 | * | 1/2005 | Giebmeyer et al. ....... 604/544 |

FOREIGN PATENT DOCUMENTS

DE     2 317 839 A     10/1974

(Continued)

*Primary Examiner*—Tatyana Zalukaeva
*Assistant Examiner*—Michael G Bogart
(74) *Attorney, Agent, or Firm*—Baker & Hostetler LLP

(57) ABSTRACT

This invention proposes a urinary catheter set with a urinary catheter disposed in a sterile package, which urinary catheter has a catheter shaft, a catheter tip and a preferably funnel-shaped end on the collecting pouch end, with a cuff being disposed in the package, which cuff encloses the catheter shaft. The cuff is preferably disposed so as to be movable along the length of the catheter shaft.

6 Claims, 2 Drawing Sheets

FOREIGN PATENT DOCUMENTS

| | | |
|---|---|---|
| EP | 0 677 299 A1 | 10/1995 |
| EP | 0 923 398 B1 | 11/2001 |
| EP | 0 959 930 B1 | 12/2002 |
| GB | 2 284 764 A * | 11/1993 |
| GB | 2 319 507 A | 5/1998 |
| WO | WO 97/26937 A1 * | 7/1997 |
| WO | WO 00/30575 | 6/2000 |

* cited by examiner

BLADDER CATHETER SET

The subject matter of the present invention relates to a urinary catheter set with a package for a urinary catheter, especially an intermediate urinary catheter, that is introduced into the urinary tube (urethra). The package sheathes the urinary catheter so as to keep it sterile. Such packages are widely known since for the intended purpose of medical instruments, they must be supplied in a sterile package. The package is broken open when the medical instrument is needed. The package ensures that the instrument contained therein remains sterile until it is used.

If the medical instrument is a catheter, the usual practice is to remove the catheter from the package when it is needed by opening the package on one end. One end of an intermediate, i.e., a short-term, urinary catheter is subsequently grasped with one hand and pulled out of the package.

To reduce the friction during catheterization, it is known to wet the external surface of the catheter with a fluid, e.g., a lubricating agent or an aqueous saline solution so as to be able to introduce the catheter as painlessly as possible and without causing further irritation to a hollow organ of the human body. It is also known to wet the external surface of a medical instrument with active medical ingredients so that these active ingredients can be delivered to the tissue adjacent to the instrument in the hollow organ.

Therefore, a urinary catheter preferably has a hydrophilic external surface along the length of its shaft, which surface, prior to opening the package, is activated by means of a fluid that is stored in a fluid reservoir disposed in the package.

The European Patents EP 0 959 930 B1 and EP 0 923 398 B1 disclose a urinary catheter set with a package for a urinary catheter integrated therein, which package also comprises a fluid reservoir that is provided for activating the hydrophilic external surface of the catheter contained in the package. The external surface of this urinary catheter is coated with a hydrophilic coating. To use the urinary catheter, it is removed from the package after the hydrophilic surface has been activated.

The disadvantage of the urinary catheter sets of the prior art is that after removal from the package, the urinary catheter, because of the length necessary for its intended use, is difficult to handle, in particular by handicapped people. Specifically, the risk involved is that by holding the catheter with one hand, its external surface may become contaminated with microorganisms. This can lead to inflammations of the urethra and the bladder, which frequently lead to complications that are at least unpleasant.

The problem to be solved by this invention is to make available a urinary catheter set with which the disadvantages of the prior art are avoided and which, in particular, is easy, fast and inexpensive to use.

This problem is solved by the device described in the independent claims. The dependent claims constitute preferred embodiments of the invention.

According to the present invention, the problem is solved by making available a catheter set for short-term catheterization which comprises a sterile package into which the urinary catheter, together with a cuff, is preferably sealed. The urinary catheter comprises a catheter shaft, a catheter tip and a preferably funnel-shaped end on the collecting pouch end. The cuff encloses the catheter shaft in at least one section. The cuff is disposed along the length of the catheter shaft so as to be movable. This has the advantage that according to the present invention the urinary catheter with the movable cuff can be inserted in a user-friendly manner. Thus, after the catheter has been removed from the package, it can be handled without directly grasping the catheter surface, i.e., by grasping only the cuff. Thus, it is possible to handle the catheter using an aseptic technique. The cuff has the advantage that sterile sections of the urinary catheter are not improperly infected by improper contact. No additional packaging measures are required.

The cuff is preferably designed as a plastic bag, which preferably has a length of 10 to 15 cm. This length is optimal for grasping the cuff with one hand since the cuff has approximately the size of a hand. The design as a plastic bag has the advantage of low manufacturing costs and a low volume, which facilitates the storage of the cuff inside the package.

The urinary catheter of the urinary catheter set according to the present invention preferably has a hydrophilic surface. Inside the package, a fluid reservoir is disposed, and the hydrophilic surface can be activated by means of a fluid stored in said fluid reservoir. The activated hydrophilic surface serves to reduce the friction during the insertion of the urinary catheter. By means of the fluid reservoir, the activation can be carried out easily and in a user-friendly manner, without the need of providing additional accessories in the urinary catheter set.

The fluid reservoir is preferably fitted with a rupture point, by means of which the fluid reservoir can be broken open while the package is closed, preferably by exerting pressure on the fluid reservoir. After breaking open the fluid reservoir, the fluid wets the surface of the catheter. This has the advantage that the activation of the hydrophilic surface can take place directly prior to the use of the catheter.

Inside the package, the fluid reservoir is preferably positioned in an area adjacent to the catheter tip so that on breaking open the fluid reservoir, a bursting of the package is avoided. This can be accomplished by ensuring that a distance of several centimeters between one end of the inner package at the catheter tip and the fluid reservoir is maintained. If the fluid reservoir were to be located directly on the end of the package, the package would run the risk of rupturing or at least of being damaged by the fluid that is under pressure, especially when the fluid reservoir is broken open by the pressure exerted.

The fluid is preferably water or preferably an 0.9 wt % saline solution or a lubricating gel. These substances have been found to be suitable for this purpose.

For use in a catheter set with a hydrophilic urinary catheter, the cuff is preferably designed so that on activation of the hydrophilic surface of the urinary catheter, the fluid collects at least partially in the cuff. The cuff encloses the catheter shaft in such a way that most of the surface of the catheter shaft is uniformly wetted with the fluid as the cuff is being moved. To facilitate this, the cuff can be designed, e.g., in the form of a plastic bag. The catheter passes through the length of the plastic bag, meaning that the plastic bag encloses the catheter shaft, with the plastic bag enclosing the catheter shaft more tightly on one end of the plastic bag than on the other end. Thus, the plastic bag forms a type of funnel with a filling opening and a discharge hole. The more tightly enclosing end is the discharge hole of the funnel, with the discharge hole enclosing the shaft of the catheter sufficiently tightly to ensure that on pushing the plastic bag into the direction of the end of the urinary catheter on the collecting pouch end, the fluid that has collected in the plastic bag can exit from the plastic bag just sufficiently to ensure that the surface of the urinary catheter is wetted with the fluid. Thus, the fluid exits from the lumen of the discharge hole, with the wetting being carried out via the volume of the lumen. This has the advantage that a uniform wetting of the catheter surface is ensured, thus in turn ensuring the most painless possible insertion of the catheter.

For the generally intended use of the catheter set, wetting the catheter shaft to fully activate the hydrophilic surface by means of the cuff is not necessary since the fluid provided for activating the hydrophilic surface can be uniformly distributed in the closed package when the fluid reservoir is broken open. The cuff primarily serves to facilitate the better handling of the catheter and to reduce the packaging material required for a safe application.

In a special embodiment of the urinary catheter set, a collecting pouch is disposed on the end of the catheter on the collecting pouch end. This makes catheterization possible even in cases in which a means for the disposal of the discharged fluid is not within reach.

The package of the urinary catheter set according to the present invention is preferably constructed of a deep-drawn film layer and a paper layer, with the urinary catheter being disposed between the deep-drawn film layer and the paper layer. Thus, an especially inexpensive and safe sterile package is provided. The paper layer has a thickness that ensures that the package is sufficiently stable. The paper is covered by a layer that ensures the sterility of the catheter and, in particular, the leakproofness of the catheter set after activation of the hydrophilic surface of the catheter, i.e., in particular after breaking open the fluid reservoir.

Preferably in the area of the collecting pouch end of the catheter (funnel area) and again preferably on an extension line of the catheter shaft, the package of the urinary catheter set has a suspension hole disposed in said area. The diameter of the suspension hole can be in the centimeter range, which makes it possible to suspend the catheter set, e.g., from a door handle. This further facilitates the handling of the catheter set.

Additional advantages follow from the description and the annexed drawings. The features of the invention mentioned earlier as well as those listed below can be used separately or in combination with one another. The embodiments mentioned are not intended as an exhaustive enumeration of possible embodiments but instead are provided merely as examples.

The invention will be explained in greater detail below using practical examples with reference to the drawings.

FIG. 1 with FIGS. 1a and 1b shows a top view and a lateral view of a catheter set according to the present invention with a urinary catheter in its package;

The figures of the drawings show the subject matter of the present invention in a highly schematic representation and are not to scale. The various components of the subject matter of the present invention are shown so as to illustrate their construction.

Figure 1A:
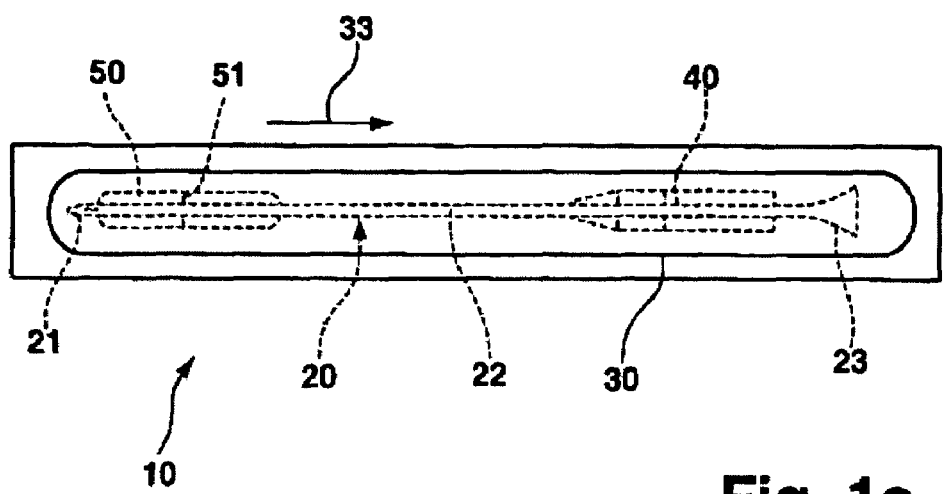
Figure 1B:
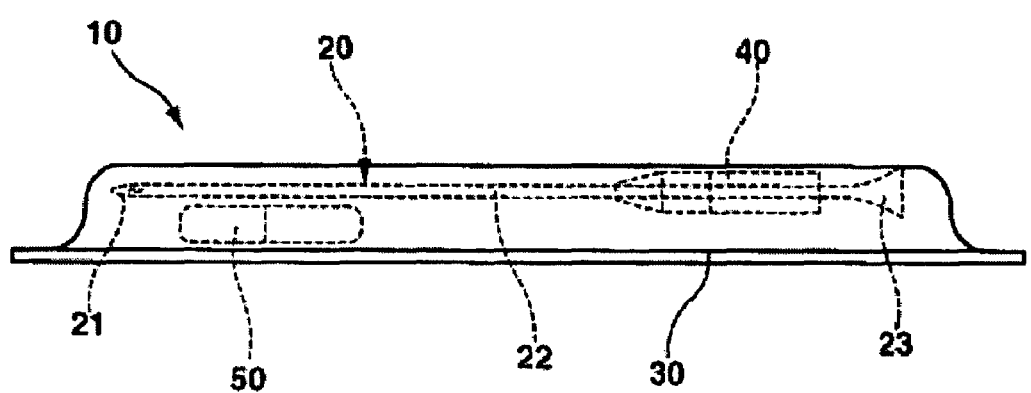

FIG. 1 shows a catheter set 10 according to the present invention with a urinary catheter 20 contained in its sterile package 30. FIG. 1a shows a top view and FIG. 1b shows a lateral view of catheter set 10. Urinary catheter 20 in its full length is contained in the package. Urinary catheter 20 has a catheter tip 21, a catheter shaft 22 and a funnel-shaped end on the collecting pouch end 23. In the package, an axially movable cuff 40 is disposed. This cuff 40 encloses the urinary catheter 20. Cuff 40 is designed as a flat-compressed plastic sheeting tube. In addition, package 30 also contains a fluid reservoir 50. Urinary catheter 20 has a hydrophilic external surface that extends along the entire length of its catheter shaft 22, and this hydrophilic external surface can be activated by means of the fluid reservoir 50, which is also integrated into the package 30. By means of a rupture point 51, fluid reservoir 50 in package 30 can be broken open. This is accomplished, e.g., by exerting pressure on fluid reservoir 50 until it ruptures. The fluid stored inside fluid reservoir 50 subsequently spreads to predetermined areas of package 30 so that the external surface of the catheter of the urinary catheter 20 stored in the package is activated across the predetermined length. In the horizontal position of the package as shown in the drawing, direction 33 in which the fluid spreads is indicated by an arrow. The fluid is preferably a physiological saline solution (0.9 wt % saline solution). Once the external surface of urinary catheter 20 has been activated, urinary catheter 20 can be removed from the package by grasping it with one hand on the collecting pouch end 23 which is designed as a funnel and by pulling urinary catheter 20 along its length out of package 30. Disposed along the length of the catheter shaft 22 is cuff 40, which may, for example, be grasped with the other hand. Cuff 40 is preferably designed so as to be movable along the length of catheter shaft 22 and constitutes an inside cover for catheter 20 so as to protect the part of the catheter that is to be inserted into the urinary tube against contamination. Cuff 40 can be pushed forward along the length of catheter shaft 22 up into the area of the tip.

Figure 2:
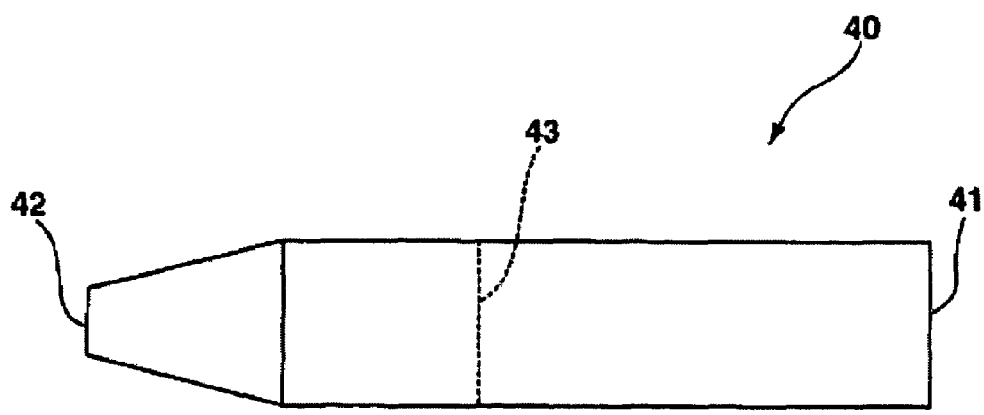
FIG. 2 shows an embodiment of a cuff of the catheter set according to the present invention.

FIG. 2 shows an embodiment of cuff 40 of the catheter set 10 according to the present invention. Cuff 40 is designed as a plastic bag which has the form of a funnel with a filling opening 41 and a discharge hole 42. The area adjacent to filling opening 41 has the form of a cylinder with a preferred length of 10 cm. Filling opening 41 preferably has a diameter of 25 to 30 mm. The cylinder-shaped area tapers into a conical section with a preferred length of 3 cm, which ends in the discharge hole 42, with a preferred diameter of 10 mm. Thus, the overall length of cuff 40 is 13 cm. The material of cuff 40 is preferably very thin and/or surface-structured. In addition, e.g., 6 cm from discharge hole 42, cuff 40 can have a perforation 43 for facilitating the tearing of cuff 40. This makes it possible to shorten cuff 40 if the user were to find this to be more convenient.

Figure 3:
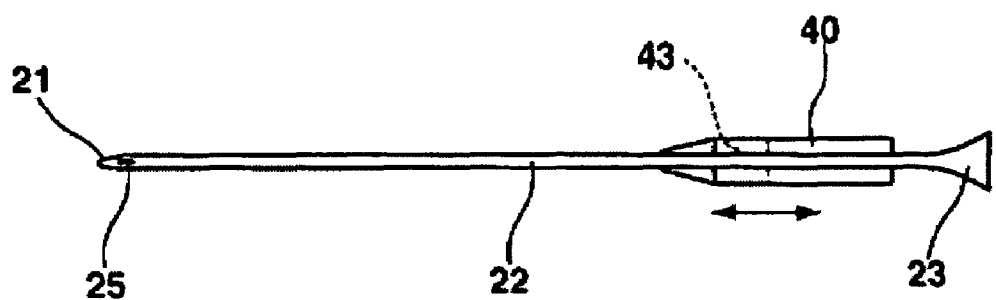
FIG. 3 shows the position of the cuff on the catheter shaft of a catheter in a catheter set according to the present invention.

FIG. 3 shows how cuff 40 that is designed as a bag is positioned on catheter shaft 22 of a catheter in a catheter set according to the present invention. The catheter, e.g., is 40 cm long. Cuff 40 can be moved along the length of the catheter, i.e., along the catheter shaft 22. At the catheter tip 21, opening 25 through which the urine can be discharged is shown. When, after activation of the hydrophilic surface of the catheter, cuff 40 is moved from catheter tip 21 along the length of catheter shaft 22 into the direction of the collecting pouch end 23 of the catheter, the surface of the catheter is uniformly wetted with the fluid used for the activation since at least part of the fluid is contained inside cuff 40, i.e., in the bag.

Figure 4:
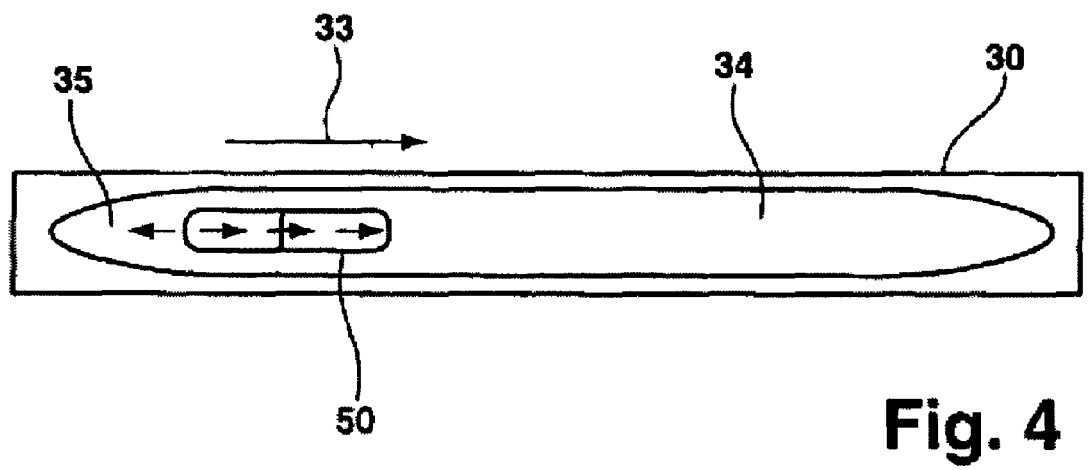
FIG. 4 shows a preferred position of the fluid reservoir of a catheter set according to the present invention.

FIG. 4 shows a preferred position of the fluid reservoir of a catheter set according to the present invention in its package. Fluid reservoir 50 is ruptured, e.g., when a force of 20 N is exerted on the fluid reservoir. This force can be generated by exerting pressure on package 30. Package 30 preferably comprises a paper layer and a deep-drawn film layer. The paper layer may also be fiber-reinforced. Using a conventional method common in packaging technology, the urinary catheter is sealed between these two layers, with the urinary catheter being disposed so as extending a cavity 34 that is formed by the deep-drawn film layer. Fluid reservoir 50 is disposed approximately 4±1 cm upstream of the catheter tip end 35 of cavity 34, i.e., in an area adjacent to the catheter tip. The space of approximately 4 cm between the fluid reservoir and the end of the cavity is provided to minimize the risk that the cavity tears or ruptures when the fluid reservoir is broken open, e.g., when it is ruptured. The direction in which the fluid stored in the fluid reservoir spreads within the cavity when fluid reservoir 50 is broken open is indicated by the arrows.

Figure 5:
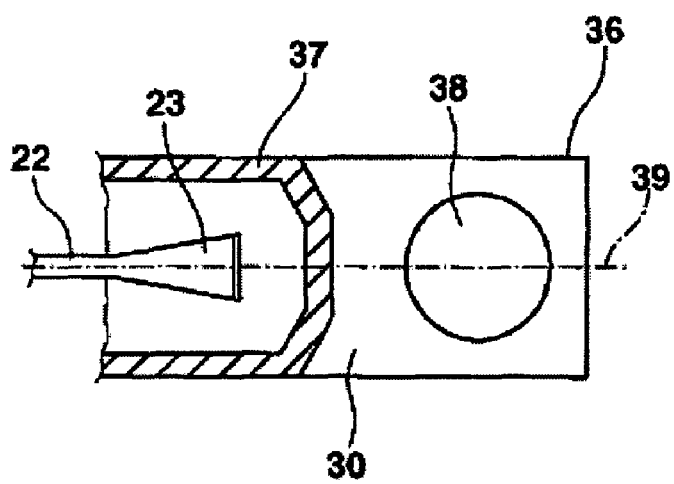
FIG. 5 shows a segment of a preferred embodiment with a suspension hole in the package of the catheter set according to the present invention.

FIG. 5 shows a preferred embodiment with a suspension hole 38 in the package of a catheter set according to the present invention. The figure shows the area of package 30 of the funnel-shaped end 23 of the catheter on the collecting pouch end. Suspension hole 38 is disposed in this area. For this purpose, the package is lengthened by approximately 4 cm in the direction of an extension line 39 of the catheter shaft beyond a sealing area 37 by means of which the paper layer is sealed to the deep-drawn film layer. Suspension hole 38, e.g., has a diameter of 2 cm and is disposed 1 cm from the heat-sealed area. The suspension hole should be disposed at least 5 mm from the edge 36 of the package.

LIST OF REFERENCE NUMERALS

10 Catheter set
20 Urinary catheter
21 Catheter tip
22 Catheter shaft
23 Collecting pouch end
25 Opening
30 Package
33 Direction in which fluid spreads
34 Cavity
35 Catheter tip end
36 Edge of package
37 Sealing area
38 Suspension hole
39 Extension line
40 Cuff
41 Filling opening
42 Discharge hole
43 Perforation
50 Fluid reservoir
51 Rupture point

The invention claimed is:

1. A urinary catheter set comprising a urinary catheter disposed in a sterile package, said catheter having a catheter shaft, a catheter tip, and a collecting pouch end, said catheter set comprising a hollow cuff which encloses a section of the catheter shaft and is disposed inside the sterile package so as to be movable along the length of the catheter shaft, and said cuff is a thin flat-compressed sheeting tube shaped to define a filling opening disposed towards the collecting pouch end and a discharge hole opposite the filling opening, the filling opening having a diameter at least double that of a diameter of the discharge hole.

2. The urinary catheter set according to claim 1, in which the urinary catheter has a hydrophilic surface, and including a fluid reservoir disposed inside the package, said fluid reservoir containing a stored fluid capable of activating said hydrophilic surface, said fluid reservoir being separate and distinct from the cuff.

3. The urinary catheter set as claimed in claim 2, in which the fluid reservoir is rupturable, while the package is closed, by exertion of pressure on the fluid reservoir, whereby said fluid completely wets the surface of the catheter after the fluid reservoir has been broken open.

4. The urinary catheter set as claimed in claim 2, in which said fluid comprises at least one substance from the group consisting of water, saline solution, and a lubricating gel.

5. The urinary catheter set as claimed in claim 2, in which said fluid comprises a 0.9 wt % saline solution.

6. The urinary catheter set as claimed in claim 2, in which said filling opening is larger than the catheter shaft at one end of the cuff, and with the discharge opening closely fitting the catheter shaft at the opposite end of the cuff, whereby, upon activation of the hydrophilic surface of the urinary catheter, the fluid is at least partially collected through said filling opening into and within the cuff, and so that upon moving the cuff along the catheter shaft, most of the surface of the catheter shaft is uniformly wetted with the fluid.

* * * * *